(12) United States Patent
Lee et al.

(10) Patent No.: US 7,141,677 B2
(45) Date of Patent: Nov. 28, 2006

(54) PEROXYOXALATE CHEMILUMINESCENCE COMPOUND AND SYSTEM

(75) Inventors: Ji Hoon Lee, Clemson, SC (US); Mark A. Schlautman, Pendleton, SC (US); Elizabeth A. Carraway, Pendleton, SC (US)

(73) Assignee: Clemson University, Clemson, SC (US)

( * ) Notice: Subject to any disclaimer, the term of this patent is extended or adjusted under 35 U.S.C. 154(b) by 192 days.

(21) Appl. No.: 10/705,586

(22) Filed: Nov. 10, 2003

(65) Prior Publication Data

US 2004/0142358 A1    Jul. 22, 2004

Related U.S. Application Data

(60) Provisional application No. 60/425,432, filed on Nov. 12, 2002.

(51) Int. Cl.
*C07D 233/14* (2006.01)

(52) U.S. Cl. .................................. 548/334.1

(58) Field of Classification Search .............. 548/334.1
See application file for complete search history.

(56) References Cited

U.S. PATENT DOCUMENTS 5,922,715 A * 7/1999 Nelson et al. .............. 514/249

OTHER PUBLICATIONS

Appelblad, et al., "Determination of C-21 Ketosteroids in Serum Using Trifluoromethanesulfonic Acid Catalyzed Precolumn Dansylation and 1,1'-Oxalyldiimidazole Postcolumn Peroxyoxalate Chemiluminescence Detection," Anal. Chem., vol. 70, No. 23, Dec. 1, 1998.*

* cited by examiner

*Primary Examiner*—Joseph K. McKane
*Assistant Examiner*—Susannah L. Chung
(74) *Attorney, Agent, or Firm*—Kennedy Covington Lobdell & Hickman, LLP

(57) ABSTRACT

An unstable, methyl-substituted (1,1 oxaly diimidazole) molecule capable of accelerating the rate at which a material attains maximum chemiluminescence when reacted hydrogen peroxide in the presence of a fluorophore and a method to synthesize such molecules.

6 Claims, 2 Drawing Sheets

OD2MI-CL REACTION

OD4MI-CL REACTION

PEROXYOXALATE CHEMILUMINESCENCE COMPOUND AND SYSTEM

This application claims priority of U.S. Provisional Patent Application No. 60/425,432, filed Nov. 12, 2002 which provisional application is herein incorporated by reference in its entirety.

PRIORITY AND ACKNOWLEDGMENT OF FEDERALLY SUPPORT

This invention was supported in part by a grant from the National Science Foundation, Grant Number 9,996,441. The Government of the United States has certain rights to practice or have practice on its behalf the claims hereof allowed.

BACKGROUND OF THE INVENTION

1. Field of the Invention

The present invention concerns generally compounds affecting the process of chemiluminescence. Specifically, the invention is related to a new compound that improves the rate at which maximum chemiluminescence is reached and the intensity of such chemiluminescence. More specifically, it relates to the synthesis of such a compound in research involving such diverse fields as clinical diagnosis (e.g. the diagnosis of cancer using specific markers) and the identification and analysis of environmental pollutants.

2. Background of the Invention

High pressure, liquid chromatographic (HPLC) systems in conjunction with a peroxyoxalate chemiluminescence system have been used to quantify fluorescent compounds at trace levels. Peroxyoxalate chemiluminescence has been used to analyze various trace fluorophores because it is more sensitive than fluorescence and UV absorbance technologies. However, with existing technology, resolution is limited by the fact that maximum chemiluminescence is attained in a matter of up to 60 seconds. Minimized separation systems including capillary electrophoresis and microchip technologies require a time frame for maximum chemiluminescence in milliseconds range. Minimizing the time to achieve maximum chemiluminescence avoids problems associated with band width instability. Therefore there remains need of and room for improvement in the compounds affecting the rate at which maximum chemiluminescence is achieved and in the half-life time of compounds driving such chemiluminescence responses.

SUMMARY OF THE INVENTION

A goal of the present invention is the provision of a high energy intermediate that generates maximum chemiluminescence in a relatively short time frame (milliseconds) compared with available technology and that provides energy transfer to drive chemiluminescence when reacting with hydrogen peroxide in the presence of a fluorophore and continues to provide energy for a relatively long half-life time. A further purpose of the invention is the provision of a compound synthesized from peroxyoxalates such as bis(2,4-dinitrophenyl)oxalate (DPNO), bis(2,4,6-trichlorophenyl)oxalate (TCPO), bis(pentachlorophenyl)oxalate (PCPO), and related compounds reacting with an imidazole derivative such as 2-methylimidazole and 4-methylimidazole to yield methyl-substituted ODI (1,1-oxaly diimidazole) molecule. A further purpose of the invention is the provision of a high energy, unstable molecule produced by reacting ODI with hydrogen peroxide, the unstable molecule being capable of transferring energy to drive chemiluminescence in a material with a fluorophore.

These and other goals and purposes of the invention are accomplished by a high energy intermediate produced from reacting peroxyoxalates with a methylimidazole and hydrogen peroxide thus producing a high energy, unstable molecule that is capable of energy transfer the maximize the rate of attaining chemiluminescence in a fluorophore and further by a system to detect low levels of substances using chemiluminescence techniques augmented by an oxylated, diimidazol compound, and still further accomplished by a method to produce a methyl substituted molecule according to the steps of adding 2-methyl imidazole in an organic solvent or mixture of organic solvents to a quantity of a peroxyoxalate at room temperature to form a high energy, unstable intermediate capable of providing energy for fluorescence.

The goals and purposes of the invention are more fully explained by reference to the accompanying figures, examples, and appended claims.

EXAMPLES

Example 1

The process to synthesize both the 1,1-oxalyl(2-methyl) diimidazole (OD2MI) and oxalyl-4-methyldiimidazole (OD4MI) molecules is carried out at room temperature (20–23C). For OD2MI, in FIG. 1A, starting with 0.5 ml of 0.4 mM bis(2,4,6 trichlorophenyl) oxalate (TCPO) 1, 0.5 ml of 8 mM 2 methylimidazole (MImH) 2 is added in ethyl acetate solvent, at a pH of 5.5 to 10.5, to yield 1 ml of OD2MI 3. The OD2MI is reacted with a quantity of 0.4 mM hydrogen peroxide 5 to yield a first, unstable, high energy intermediate 6. The first, high energy, unstable intermediate is capable of transferring energy to generate chemiluminescence in 0.5 ml of material with fluorescing molecules to cause the rapid attainment of maximum fluorescence.

Example 2

Figure 1A:
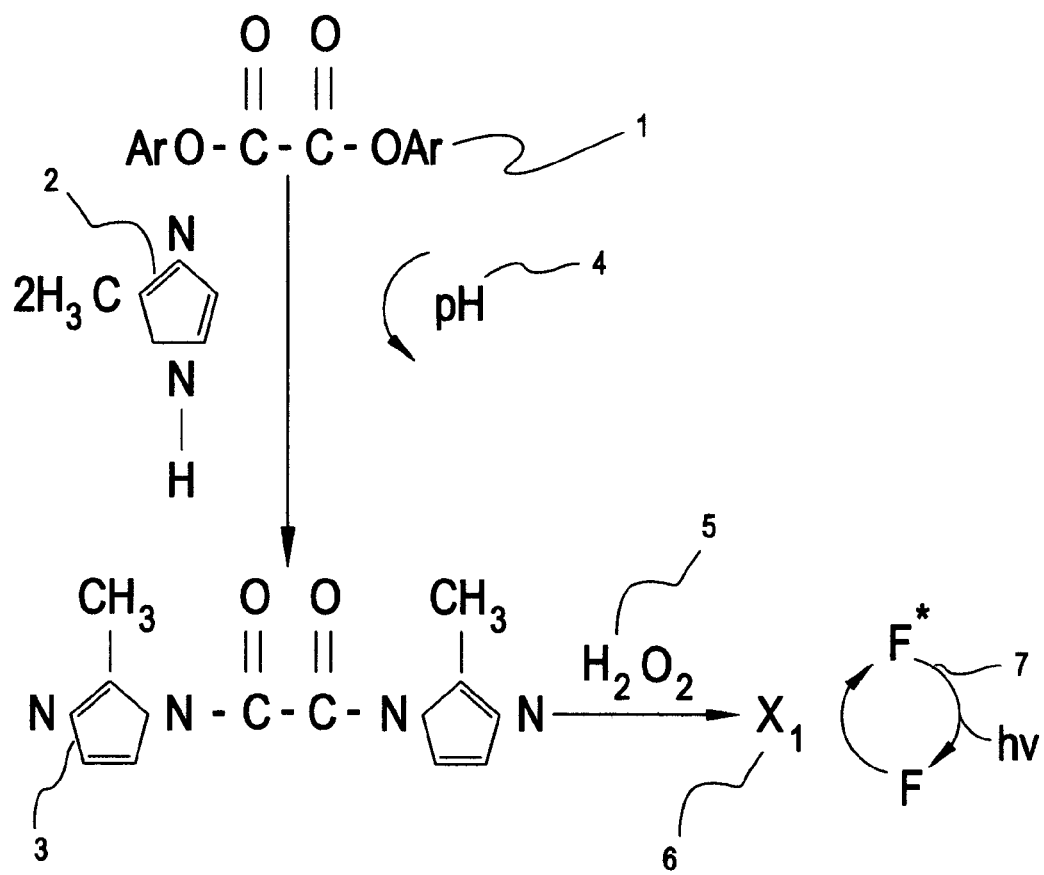
FIG. 1A illustrates the synthesis of OD2MI and the subsequent chemiluminescence reaction.
Figure 1B:
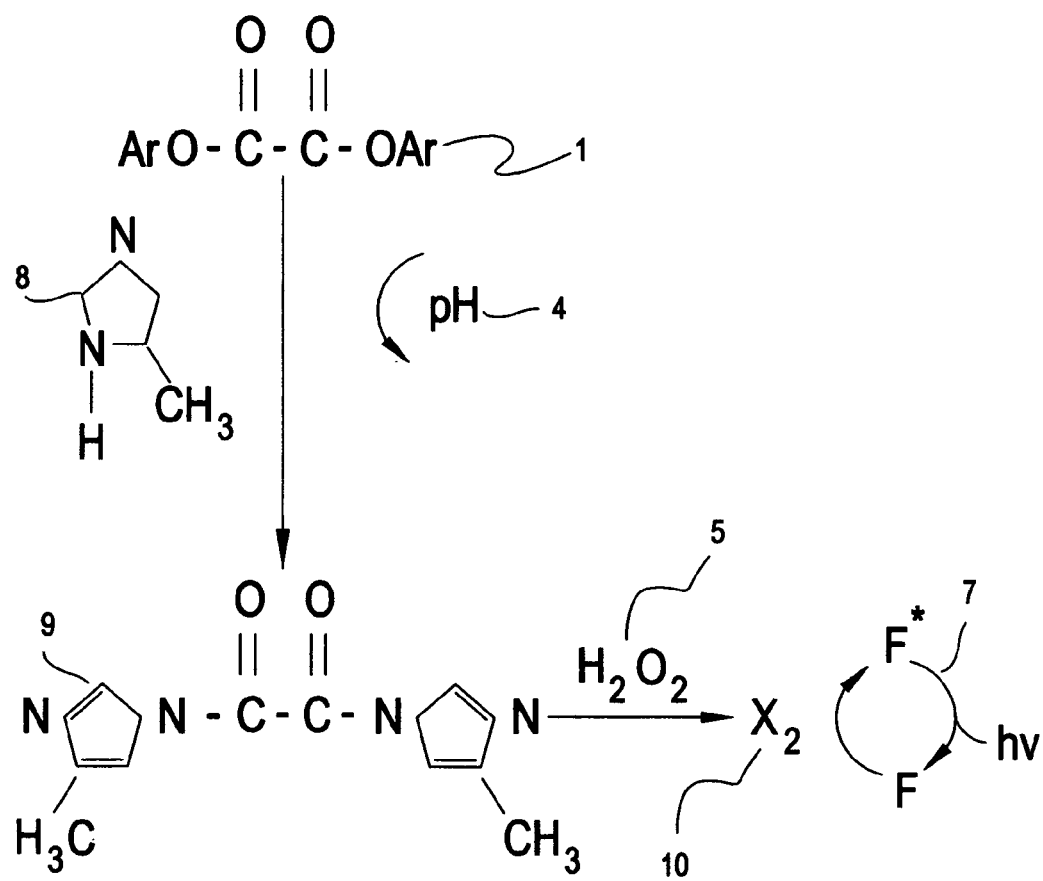
FIG. 1B illustrates the synthesis of OD4MI and the subsequent chemiluminescence reaction.

From FIG. 1B, OD4MI 9 is synthesized in a manner effectively identical to that described for the synthesis OD2MI; recall FIG. 1A. At room temperature, starting with 0.5 ml of 0.4 mM of (TCPO) 1, 0.5 ml of 8 mM 4 methylimidazole (4MImH) 8 is added in ethyl acetate solvent at a pH from 5.5 to 10.5 to yield 1 ml of OD4MI 9. The (OD4MI) 9 is reacted with a quantity of 40 mM hydrogen peroxide 5 to yield a second unstable, high energy molecule 10. This second, high energy, unstable molecule is capable of transferring energy to generate chemiluminescence in 0.5 ml of material with fluorescing molecules to cause the rapid attainment of maximum fluorescence.

Example 3

Comparisons of three oxalyldiimidazole derivatives for four traits reflect the effects of the OD2MI and OD4MI reactions. The three compounds were the prior ODI control, the OD2MI of Example 1, and the OD4MI of Example 2.

The four traits evaluated are reaction time (time between TCPO and ImH derivative (ImH, 2MImH, and 4MImH) to form maximum concentrations of ODI derivatives), I max (the maximum CL intensity), T max (maximum time seconds), and half-life of the unstable compound, seconds). For ODI the respective values are 120, 31.1, 0.6, and 2.4, respectively. For OD2MI the corresponding values are 180, 15.6, 0.5, and 7.2. And for OD4MI the values are 45, 61.1, 0.5, and 2.9. The problem of band broadening common in PO-CL detection is solved as illustrated by the above data by means of a very fast CL reaction pathway characteristic of the ODI-CL reaction described in examples 1 and 2 above.

The above results are summarized from studies of environmental toxins. Amino- and nitro-polycyclic aromatic hydrocarbons (PAHs) are important environmental contaminants that are generally more toxic (eg. mutagenic, carcinogenic) than their respective parents PAH parent compounds. Although peroxyoxalate chemiluminescence (PO-CL) detection combined with chromatographic separation has been widely advocated for the environmental analysis of PAHs, its potential for detecting amino- and nitro-PAHs is not known. In the presence of hydrogen peroxide, (10.0 mM) and TCPO (0.1 mM) the maximum CL of 1-aminopyrene in base-catalyzed nucleophilic CL reactions follows a trend consistent with the pKa ordering of the base catalysts 2-MImH>4MImH>ImH. Maximum CL in the presence of 2MImH (2-MImH-catalyzed reaction) was 1.8 and 4.5 times larger than in the presence of 4-MimH and ImH, respectively. Maximum CL of 1-aminopyrene for the reaction between OD4MI and hydrogen peroxide was 2.4 and 8.0 larger than that for the reactions between ODI and OD2MI and hydrogen peroxide. In addition, maximum CL and the time to reach the maximum emission(T max=0.4 sec) of 1-aminopyrene in the reaction between OD4MI and hydrogen peroxide were about 60 times larger and 12 times faster, respectively, than those in the ImH-catalyzed nucleophilic condition that have been reported for PAH determinations. PL-CL detections techniques demonstrate super qualities with respect to detecting low concentrations of a variety of compounds and substances.

What is claimed is:

1. A molecule capable of transferring energy to maximize a rate of attaining chemiluminescence in a fluorophore, wherein said molecule is formed from reacting 1,1-oxalyl (2-methyl)diimidazole (OD2MI) with hydrogen peroxide.

2. A molecule capable of transferring energy to maximize a rate of attaining chemiluminescence in a fluorophore, wherein said molecule is formed from reacting oxalyl(4-methyl)diimidazole (OD4MI) with hydrogen peroxide.

3. A method to produce a methyl substituted molecule comprising the steps of: adding a quantity of 2-methylimidazole in an acetate solvent to a quantity of bis(2,4,6 trichiorophenyl) oxylate thereby yielding a methyl substituted oxylate, then reacting said methyl substituted oxalate with a quantity of hydrogen peroxide thereby producing a high energy, unstable molecule, and finally collecting said high energy, unstable molecule for use to provide energy for fluorescence.

4. The method of claim 3 wherein the pH is in the range of 5.5 to 10.5.

5. The method of claim 3 wherein said methyl substituted molecule is OD2MI.

6. The method of claim 3 wherein said methyl substituted molecule is OD4MI.

* * * * *